US009655603B2

(12) United States Patent
Tegels et al.

(10) Patent No.: US 9,655,603 B2
(45) Date of Patent: May 23, 2017

(54) AUTOMATIC SEALANT DELIVERY CATHETER RETRACTION FOR VASCULAR CLOSURE DEVICE AND METHODS

(71) Applicant: St. Jude Medical Puerto Rico LLC, Caguas, PR (US)

(72) Inventors: Zachary J. Tegels, Minneapolis, MN (US); Catherine A. Pipenhagen, Chanhassen, MN (US); Edward E. Parsonage, St. Paul, MN (US); Russell D. Terwey, St. Michael, MN (US); Martha Escobar, Jordan, MN (US); Robert M. Vidlund, Forest Lake, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 533 days.

(21) Appl. No.: 13/778,529

(22) Filed: Feb. 27, 2013

(65) Prior Publication Data

US 2014/0135823 A1    May 15, 2014

Related U.S. Application Data

(60) Provisional application No. 61/726,405, filed on Nov. 14, 2012.

(51) Int. Cl.
*A61B 17/00* (2006.01)
*A61B 17/22* (2006.01)

(52) U.S. Cl.
CPC .. *A61B 17/0057* (2013.01); *A61B 2017/0065* (2013.01); *A61B 2017/00623* (2013.01);
(Continued)

(58) Field of Classification Search
CPC ...... A61B 17/0057; A61B 2017/00623; A61B 2017/0065; A61B 2017/00654; A61B 2017/22067
See application file for complete search history.

(56) References Cited

U.S. PATENT DOCUMENTS 6,090,130 A * 7/2000 Nash ................. A61B 17/0057
604/168.01
8,333,787 B2    12/2012 Pipenhagen et al.
(Continued)

FOREIGN PATENT DOCUMENTS

WO    2005092204 A2    10/2005

OTHER PUBLICATIONS

PCT International Search Report for International Application No. PCT/US2013/027845, mailed Oct. 16, 2013 (6 pp.).
(Continued)

*Primary Examiner* — Thomas McEvoy
(74) *Attorney, Agent, or Firm* — Holland & Hart

(57) ABSTRACT

A vessel puncture closure device includes a balloon catheter and a sealant delivery device. The balloon catheter has an inflatable balloon positioned at a distal end thereof. The sealant delivery catheter has a sealant lumen configured to delivery a volume of sealant to a vessel puncture. The sealant delivery catheter is configured to move axially relative to the balloon between a first position in which the sealant delivery catheter delivers a first volume of sealant to the vessel puncture, and a second position spaced proximal of the first position to deliver a second volume of sealant to the vessel puncture.

15 Claims, 15 Drawing Sheets

(52) U.S. Cl.
CPC .............. *A61B 2017/00654* (2013.01); *A61B 2017/22067* (2013.01)

(56) References Cited

U.S. PATENT DOCUMENTS

| | | | |
|---|---|---|---|
| 8,506,592 B2 | 8/2013 | Killion et al. | |
| 2004/0267308 A1* | 12/2004 | Bagaoisan et al. | 606/213 |
| 2011/0166595 A1 | 7/2011 | Vidlund et al. | |
| 2011/0282383 A1 | 11/2011 | Vidlund et al. | |
| 2013/0006299 A1 | 1/2013 | Pipenhagen et al. | |
| 2013/0190808 A1 | 7/2013 | Tegels et al. | |
| 2013/0190812 A1 | 7/2013 | Vidlund | |
| 2013/0190813 A1 | 7/2013 | Tegels et al. | |

OTHER PUBLICATIONS

U.S. Appl. No. 13/770,586, filed Feb. 19, 2013.
U.S. Appl. No. 13/770,714, filed Feb. 19, 2013.
U.S. Appl. No. 13/772,834, filed Feb. 21, 2013.
U.S. Appl. No. 13/773,062, filed Feb. 21, 2013.
U.S. Appl. No. 13/773,206, filed Feb. 21, 2013.

* cited by examiner

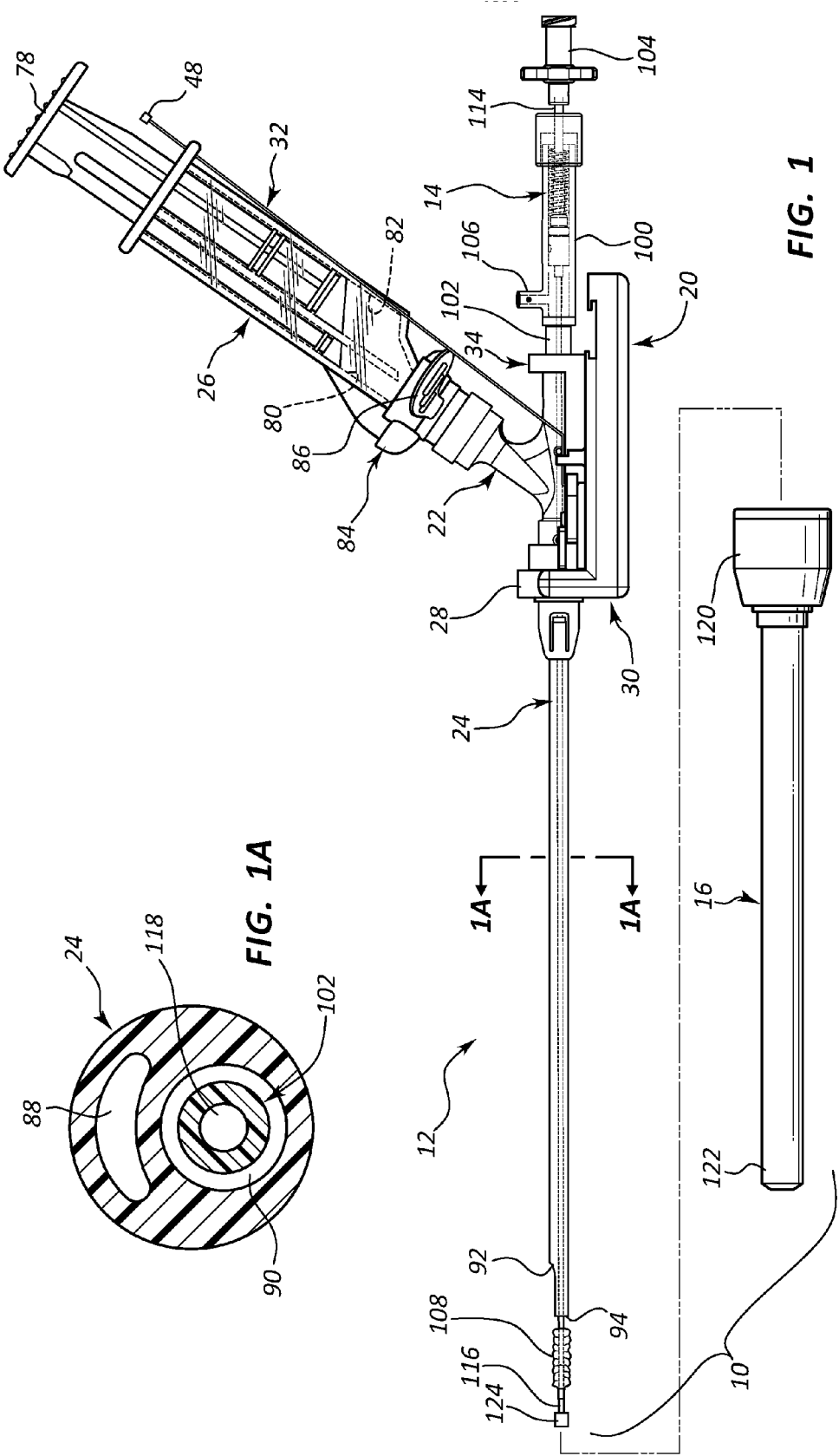

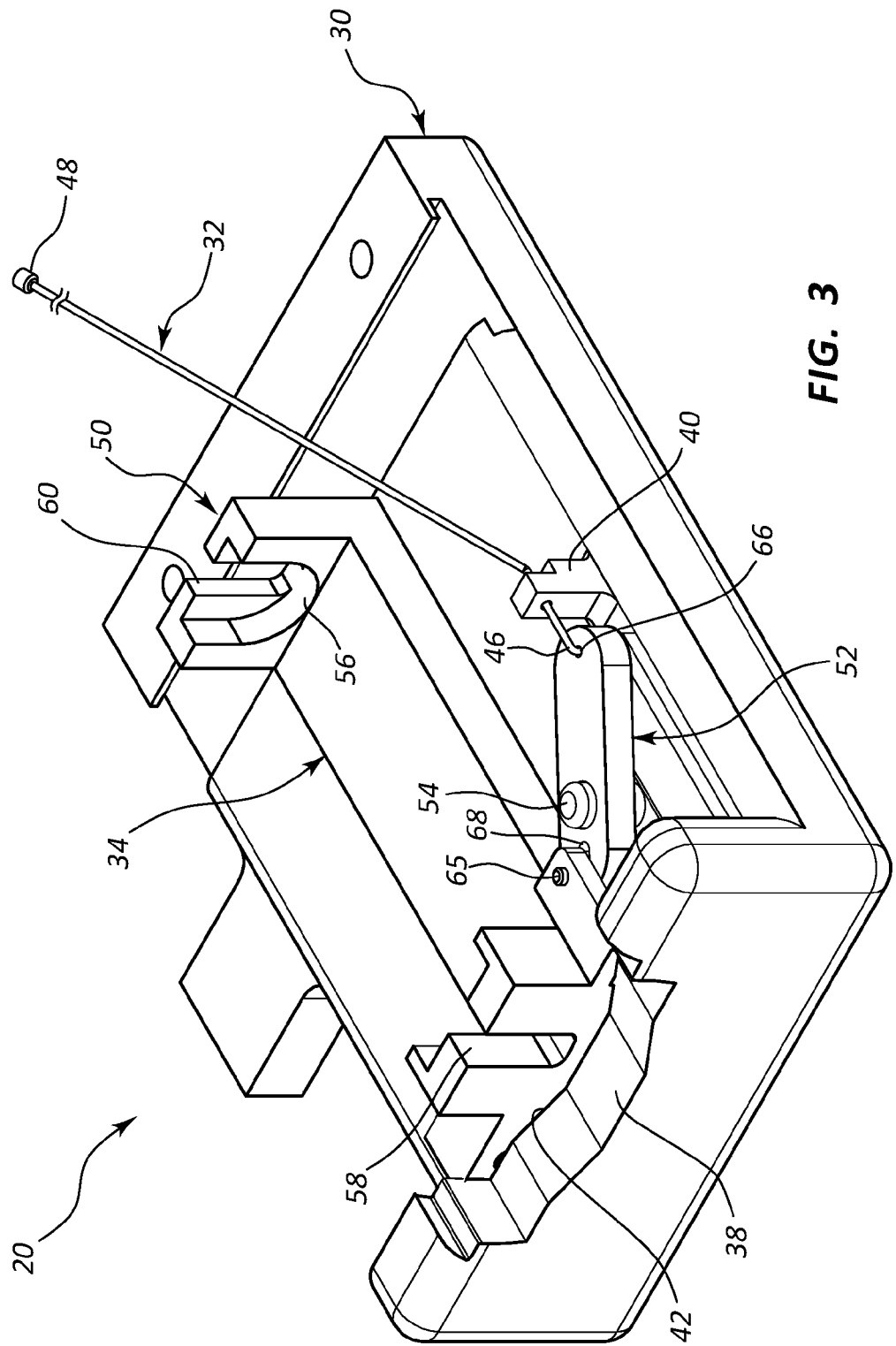

AUTOMATIC SEALANT DELIVERY CATHETER RETRACTION FOR VASCULAR CLOSURE DEVICE AND METHODS

CROSS-REFERENCE TO RELATED APPLICATION

This application claims the benefit of the filing date of U.S. Provisional Application No. 61/726,405, filed Nov. 14, 2012, and entitled AUTOMATIC SEALANT DELIVERY CATHETER RETRACTION FOR VASCULAR CLOSURE DEVICE AND METHODS, the disclosure of which is incorporated, in its entirety, by reference.

TECHNICAL FIELD

The present disclosure relates generally to methods and systems for sealing tissue punctures, and more particularly, to methods and systems for delivering sealant to tissue punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while maintaining the temporary seal from the balloon. Challenges exist in delivering a volume of flowable sealing material to the tissue puncture to seal the tissue puncture.

SUMMARY

One aspect of the present disclosure relates to a vessel puncture closure device that includes a balloon catheter and a sealant delivery device. The balloon catheter has an inflatable balloon positioned at a distal end thereof. The sealant delivery catheter has a sealant lumen configured to delivery a volume of sealant to a vessel puncture. The sealant delivery catheter is configured to move axially relative to the balloon between a first position in which the sealant delivery catheter delivers a first volume of sealant to the vessel puncture, and a second position spaced proximal of the first position to deliver a second volume of sealant to the vessel puncture.

The vessel puncture closure device may include a retraction device interposed between the balloon catheter and sealant delivery catheter to move the sealant delivery device between the first and second positions. The retraction device may include an activator, which when operated causes the retraction device to automatically move the sealant delivery catheter between the first and second positions. The sealant delivery device may include a distal sealant opening spaced a first predetermined distance from the balloon in the first position and spaced a second predetermined distance from the balloon in the second position. The refraction device may include a biasing member, and releasing the biasing member moves the sealant delivery catheter between the first and second positions.

The vessel puncture closure device may include a sealant source coupled in flow communication with the sealant delivery device, and operating the sealant source to deliver one of the first and second volumes of sealant operates the retraction device. The sealant source may include a syringe having a plunger, and operating the plunger to eject at least one of the first and second volumes of sealant into the sealant delivery device operates the refraction device. The sealant delivery device may be advanced over the balloon inflation device to the vessel puncture. The balloon catheter may include a housing, and the retraction device is mounted to the housing. The vessel puncture closure device may include a detachable sealing tip positioned at a distal end of the balloon inflation device distal of the balloon, wherein the detachable sealing tip is detachable within the first volume of sealant upon removal of the balloon inflation device from the vessel puncture.

Another aspect of the present disclosure relates to a tissue puncture closure device that includes first and second catheters and a retraction device. The first catheter includes a balloon positioned at a distal end thereof and is insertable through a tissue puncture. The first catheter is configured to inflate the balloon to temporarily seal the tissue puncture internally. The second catheter is configured to advance over the first catheter to the tissue puncture and deliver a volume of sealant to seal the tissue puncture externally. The retraction device is operable between the first and second catheters to automatically move a distal opening of the sealant delivery device between a first axial position relative to the balloon and a second axial position spaced further from the balloon than the first axial position.

The retraction device may include a trigger operable to actuate the refraction device. The tissue puncture closure device may include a sealant source configured to deliver a first volume of sealant to the tissue puncture when the distal opening is in the first axial position, and to deliver a second volume of sealant to the tissue puncture when the distal opening is in the second axial position. Operating the sealant source may actuate the trigger. The sealant source may operate to provide a continuous flow of the first and second volumes of sealant.

Another aspect of the present disclosure relates to a method of sealing a vessel puncture. The method includes providing a balloon catheter having an inflatable balloon positioned at a distal end thereof, a sealant delivery catheter configured to deliver a volume of sealant to a vessel puncture, and a retraction device. The method includes inserting the inflatable balloon through the vessel puncture and inflating the balloon to temporarily seal the vessel puncture, advancing the sealant delivery device over the balloon catheter to a first position relative to the vessel puncture, delivering a first volume of sealant through the sealant delivery device to the vessel puncture, operating the retraction device to automatically move the sealant delivery device to a second position relative to the vessel puncture, and delivering a second volume of sealant through the sealant delivery device to the vessel puncture.

Operating the retraction device may include releasing a biasing member. Automatically moving the sealant delivery device to a second position relative to the vessel puncture may include moving the sealant delivery device axially to a position further away from the vessel puncture. The method may include providing a sealant source configured to provide the first and second volumes of sealant to the sealant delivery device, wherein operating the sealant source actuates the retraction device. The method may include deflating the balloon and removing the balloon catheter through the first and second volumes of sealant delivered to the vessel puncture.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure system in accordance with the present disclosure.

FIG. 1A is a cross-sectional view of a vascular closure device of the vascular closure system of FIG. 1 taken along cross-section indicators 1A-1A.

FIG. 3 is a perspective view of a retraction assembly of the vascular closure device of FIGS. 1 and 2A in a pre-ejection position.

Throughout the drawings, identical reference numbers designate similar, but not necessarily identical, elements.

DETAILED DESCRIPTION

Figure 2A:
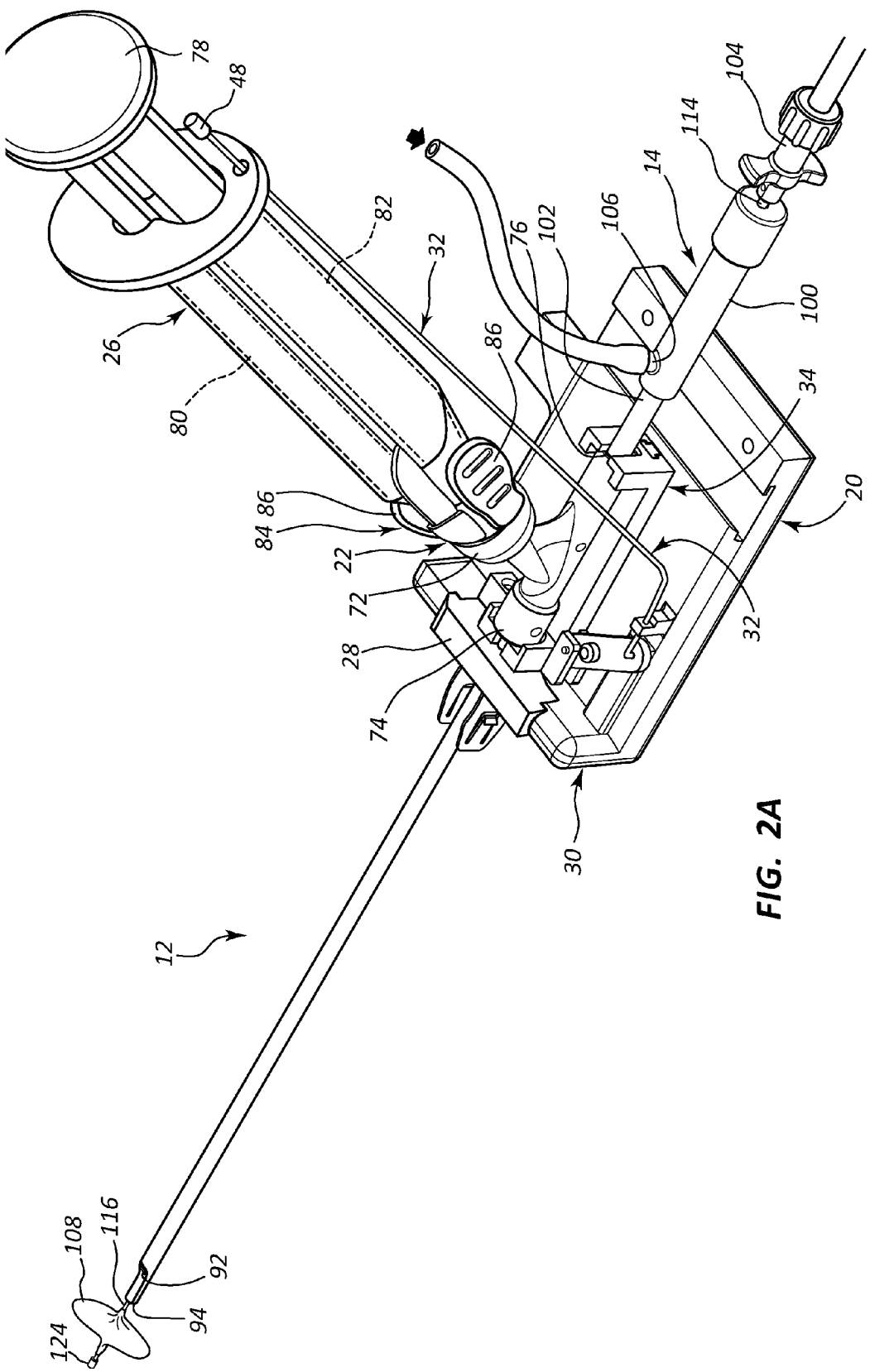
FIG. 2A is a side view of a vascular closure device and a balloon location device of the vascular closure system of FIG. 1 in a pre-ejection position.

The systems disclosed herein may be used to close or seal percutaneous punctures made through the body tissue of a patient to gain access to a body cavity of the patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure includes a vascular closure device operable to deliver a volume of sealant to a tissue puncture. The vascular closure device may be used in cooperation with a balloon location device and sheath as part of a vascular closure system. One aspect of the present disclosure relates to features of the vascular closure system that provide automatic retracting of the vascular closure device during delivery of the sealant to the tissue puncture. The system operates to provide delivery of the sealant immediately onto a surface of the tissue puncture (i.e., vascular puncture) and surrounding areas at a distal end of a tissue tract that leads to the tissue puncture. The system further operates to automatically retract within the tissue tract to deposit more of the sealant within the tissue tract for additional coverage and sealing.

One benefit of the auto-retraction feature of the vascular closure system is the ability to deposit a greater amount of sealant within the tissue tract in a more controlled manner. Another benefit relates to creation of a more even flow of sealant within the tissue tract and tissue puncture. A further benefit relates to formation of a sealant plug within the tissue puncture and tissue tract having a greater longitudinal length. The increased length for the plug may assist in supporting a detachable sealing tip within the tissue tract for additional sealing of the tissue puncture and sealant plug upon removal of the vascular closure device through the sealant plug.

The automatic retraction of the vascular closure device may occur automatically in response to depressing a syringe plunger or other feature of a sealant delivery device to deliver a volume of sealant to the tissue puncture. Other features may be used to create the auto-retraction including, for example, buttons, levers, switches, etc. that may be actuated manually by an operator independent of delivery of the sealant. In one example, the automatic retraction may occur by releasing a biasing member (e.g., spring) or a linear coupling that provides linear movement of the vascular closure device relative to the tissue tract and other features of the vascular closure system (e.g., an inflatable balloon that acts as an anchor and temporary seal of the tissue puncture at a location distal of the tissue puncture).

In some arrangements, the automatic retraction may be invisible to the operator. For example, operating the vascular closure system to deliver a volume of sealant to the tissue puncture may create actuation of the automatic retraction after delivery of a predetermined volume of the sealant at the tissue puncture.

Referring now to FIGS. 1-5, an example vascular closure system 10 having an automatic retraction feature is shown and described. The vascular closure system 10 includes a vascular closure device 12, a balloon location device 14, and a sheath 16 (see FIGS. 1 and 2A-2C). The balloon location device 14 is inserted through the vascular closure device 12 to position a balloon carried by the balloon location device 14 at a location distal of a distal end of the vascular closure device 12. The vascular closure device 12 and balloon location device 14 are typically inserted through the sheath 16 as part of treating a tissue puncture as will be described in further detail below. The sheath 16 may be used to access the tissue puncture and provide an open path through the tissue puncture. The sheath 16 may extend through the tissue puncture to a lumen such as a vessel lumen positioned distal of the tissue puncture.

The vascular closure device 12 may include a retraction assembly 20, a manifold 22, a delivery tube 24, a primary sealant device 26, and a latch 28. The manifold 22 is typically releasably mounted to the retraction assembly 20. A delivery tube 24 is connected in fluid communication with the manifold 22. The primary sealant device 26 is connected to the manifold 22 and provides a source of sealant for delivery through the manifold 22 and delivery tube 24 to the tissue puncture. The latch 28 may be mounted to at least one of the manifold 22, the delivery tube 24, and retraction assembly 20. The latch 28 may provide a positive attachment with the sheath 16. Typically, a portion of the retraction assembly (i.e., a base) is fixed relative to the sheath 16, while other portions of the retraction assembly (i.e., a carriage assembly) are axially moveable relative to the sheath 16. Further, a delivery tube 24 is typically mounted to a portion of the retraction assembly 20 (i.e., the carriage assembly 34) while being axially moveable relative to another portion of the retraction assembly (i.e., the base 30).

Figure 4:
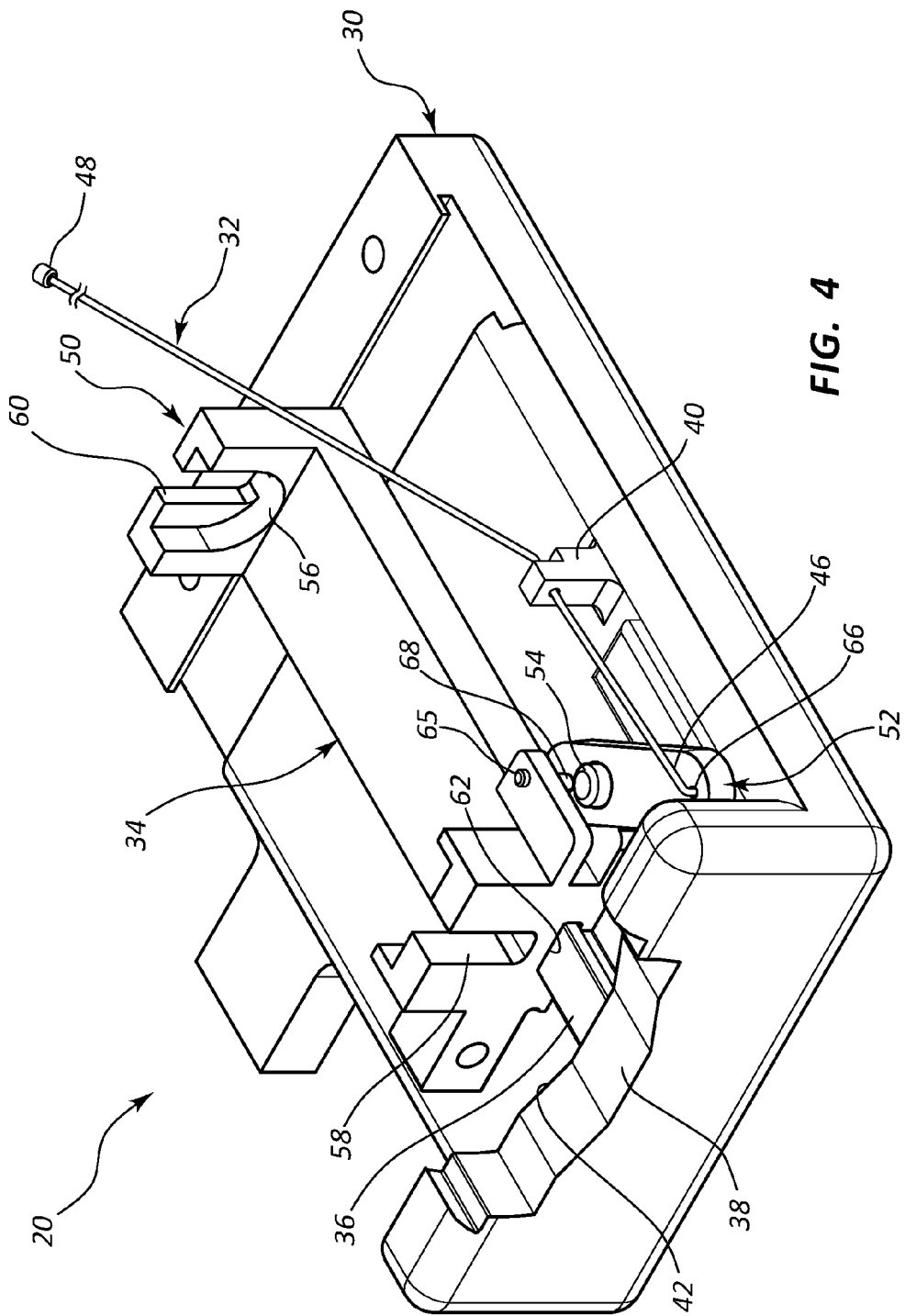
FIG. 4 is a perspective view of the retraction assembly of FIG. 3 in a retracted or second ejection position.
Figure 5:
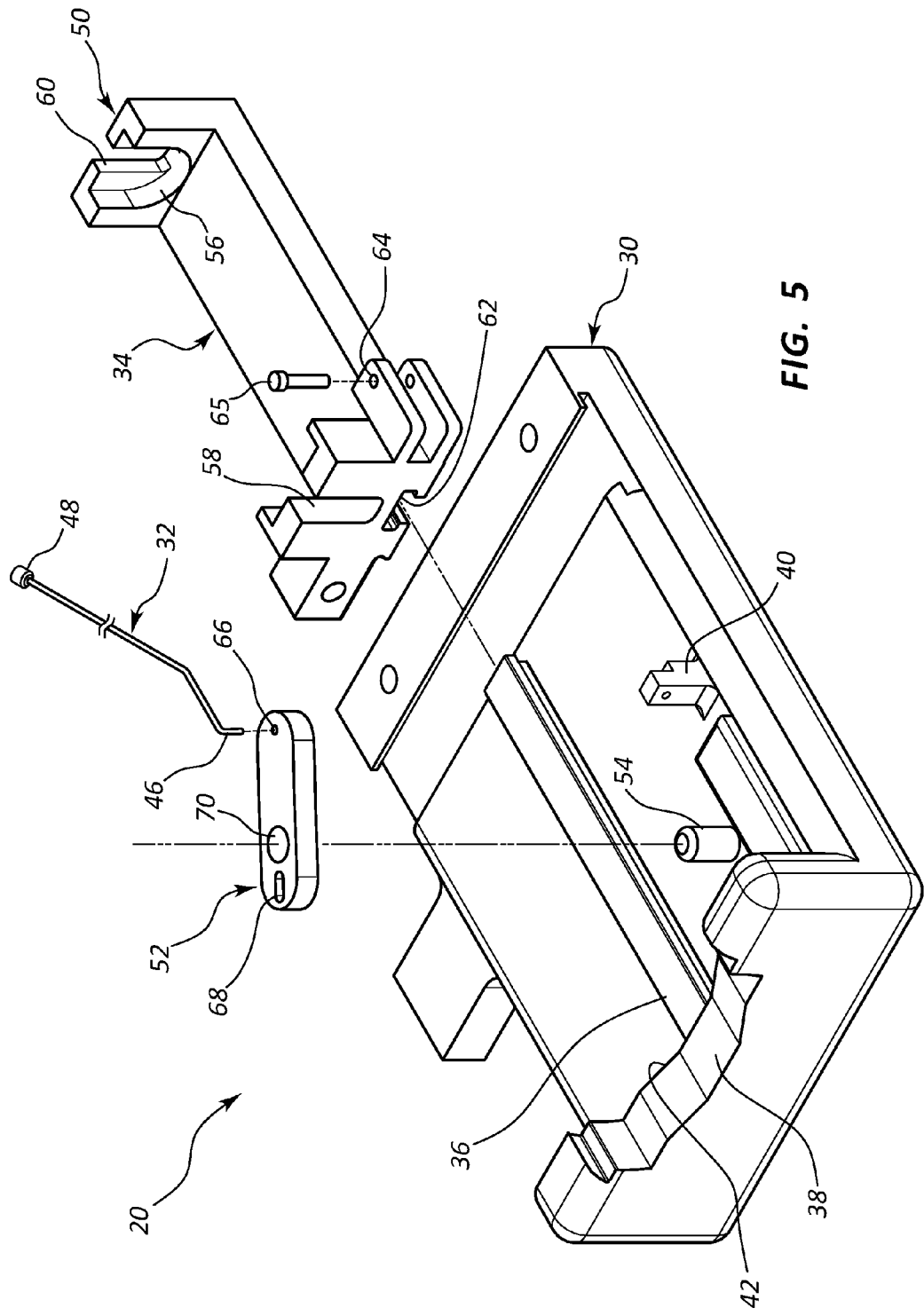
FIG. 5 is an exploded perspective view of the refraction assembly of FIGS. 3 and 4.

Referring to FIGS. 3-5, the retraction assembly 20 includes a base 30, a wire 32, and a carriage assembly 34. The base supports the carriage assembly 34 and the carriage assembly 34 moves longitudinally relative to the base 30. The base 30 is typically connected to the sheath 16 and the carriage assembly 34 is typically connected to the delivery tube 24. The carriage assembly 34 may move longitudinally relative to the balloon location device 14.

The base 30 includes a base track 36 (see FIG. 4), a latch seat 38, a wire support 40, and a carriage stop 42 (see FIG. 5). The carriage assembly 34 is connected to the base 30 at the base track 36. The base track 36 provides longitudinal movement of the carriage assembly 34 relative to the base 30. The latch 28 is connected to the base 30 at the latch seat 38. The latch 28 may be releasably mounted to the base 30. In some arrangements, the vascular closure device 12 does not include a latch 28 and may not have a positive connection to sheath 16.

The wire support 40 may provide a guide that supports the wire 32. The wire support 40 may be mounted to base 30 and include an aperture through which a portion of wire 32 extends. Carriage stop 42 may be defined in part by the structure forming latch seat 38. Carriage top 42 may provide a position stop for the carriage assembly 34 relative to base 30 in a distal direction.

Wire 32 may include a distal connector 46 and a proximal end 48. The distal connector 46 may be connected to a portion of carriage assembly 34 such as, for example, a lever that provides relative movement between the carriage assembly 34 and base 30. The proximal end 48 of wire 32 may extend proximally to a position where proximal end 48 is contacted during operation of the vascular closure device 12 (e.g., operating the primary sealant device 26 to deliver a volume of sealant). In one example, the proximal end 48 is contacted by a plunger portion of the primary sealant device 26 after the plunger has moved distally a predetermined distance to deliver a first volume of sealant. Further operation of the plunger advances the wire 32 to actuate the carriage assembly 34.

Carriage assembly 34 includes a carriage 50, a lever 52, and a lever pin 54. Carriage 50 includes a manifold seat 56, a distal tube opening 58, a proximal tube opening 60, a carriage track 62, and a lever attachment point 64. The carriage 50 is connected to base 30 at the carriage track 62. Manifold 22 is connected to carriage assembly 34 at the manifold seat 56. The manifold 22 may be connected to manifold seat 56 with, for example, a snap-fit connection, a fastener, adhesives, or other connection features. A delivery tube 24 extends into the carriage assembly 34 through the distal tube opening 58. A portion of the balloon location device 14 extends into carriage assembly 34 through the proximal tube opening 60.

Lever 52 is pivotally mounted to base 30 with the lever pin 54. Lever pin 54 extends through a pin mounting hole 70 of lever 52. One end of lever 52 includes a wire attachment point 66 wherein the distal connector 46 of wire 32 is connected. An opposite end of lever 52 includes a carriage attachment point 68 wherein lever 52 is connected to the lever attachment point 64 of carriage 50 with a connecting pin 65.

The carriage assembly is operable by operation of wire 32 to move carriage 50 from an advanced position shown in FIG. 3 to a retracted position shown in FIG. 4. The advanced position may be determined at least in part by the carriage stop 42. In one example, the retracted position is defined at least in part by a maximum rotated position of lever 52 by advancing wire 32. In other examples, the retracted position may be defined by a stop feature (not shown) positioned on base 30 that is contacted by carriage 50.

In operation, the carriage 50 is positioned in the advanced position shown in FIGS. 1 and 3. Advancing a plunger 78 of primary sealant device 26 delivers a first volume of sealant to the tissue puncture. Further advancing plunger 78 contacts the proximal end 48 of wire 32, which rotates lever 52 to retract carriage 50 relative to base 30. Retraction of carriage 50 withdraws the delivery tube 24 within the tissue tract 138 so that further delivery of sealant to the tissue puncture continues to fill the tissue tract.

Referring again to FIGS. 1 and 2A-2C, the manifold 22 includes an injection port 72, and distal and proximal openings 74, 76. The primary sealant device 26 is connected to the manifold 22 at the injection port 72. The delivery tube 24 is connected to the distal opening 74 of manifold 22. The balloon location device 14 is inserted through the proximal opening 76 of manifold 22.

The delivery tube 24 includes first and second lumens 88, 90. The first lumen 88 includes a distal opening 92. Second lumen 90 includes a distal opening 94.

Primary sealant device 26 includes a plunger 78, first and second chambers 80, 82, and an adapter 84. The first and second chambers 80, 82 carry sealant components for the sealant material ejected from the primary sealant device 26. The sealant components may include, for example, an activator and a precursor. The sealant components carried in the first and second chambers 80, 82 may have quick-set properties when mixed together.

The adaptor 84 may be interposed between the first and second chambers 80, 82 and the injection port 72 of manifold 22. Adaptor 84 may include a plurality of fluid channels that direct the sealant components from the first and second chambers 80, 82 to the injection port 72 of manifold 22. Adapter 84 may also include release tabs 86 that facilitate connection of primary sealant device 26 to manifold 22.

Balloon location device 14 includes a housing 100, an inner tube 102, an inner tube manifold 104, an inflation fluid port 106, a balloon 108 and a detachable tip 124. The inner tube 102 may extend distally from housing 100 and be sized for insertion through manifold 22 and delivery tube 24 to position balloon 108 distal of delivery tube 24. Inner tube 102 may include proximal and distal ends 114, 116, and a lumen 118 (see FIG. 1A). The balloon 108 may be inflated using a volume of inflation fluid provided through one of the second lumen 90 and delivery tube 24 or the lumen 118 of inner tube 102.

The detachable tip 124 may be carried at the distal end 116 of inner tube 102. The detachable tip 124 may be detached within the volume of sealant that is used to seal the tissue puncture as described below with reference to FIG. 12.

Figure 2B:
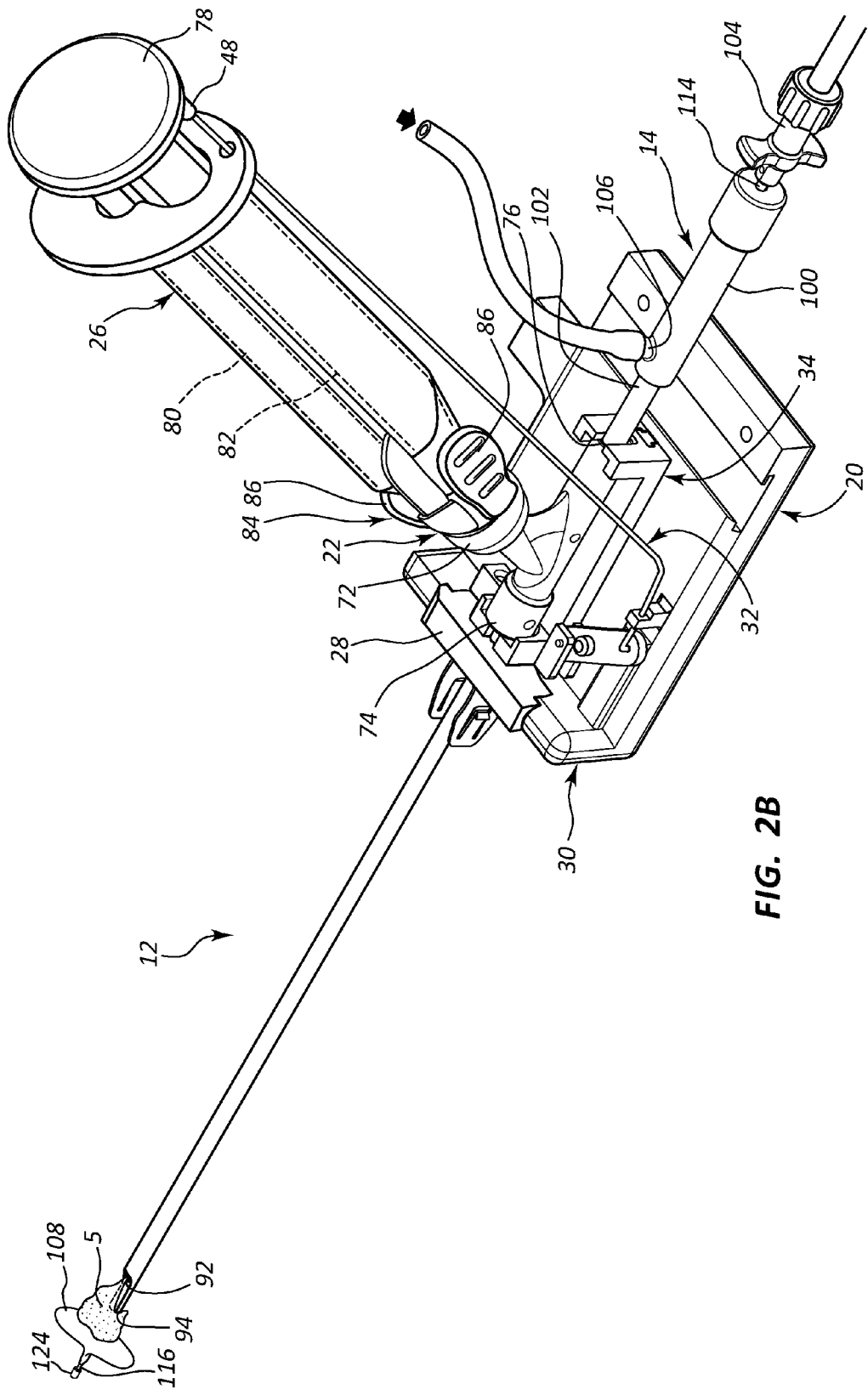
FIG. 2B is a side view of the vascular closure device and balloon location device of FIG. 2A in a first ejection position.
Figure 2C:
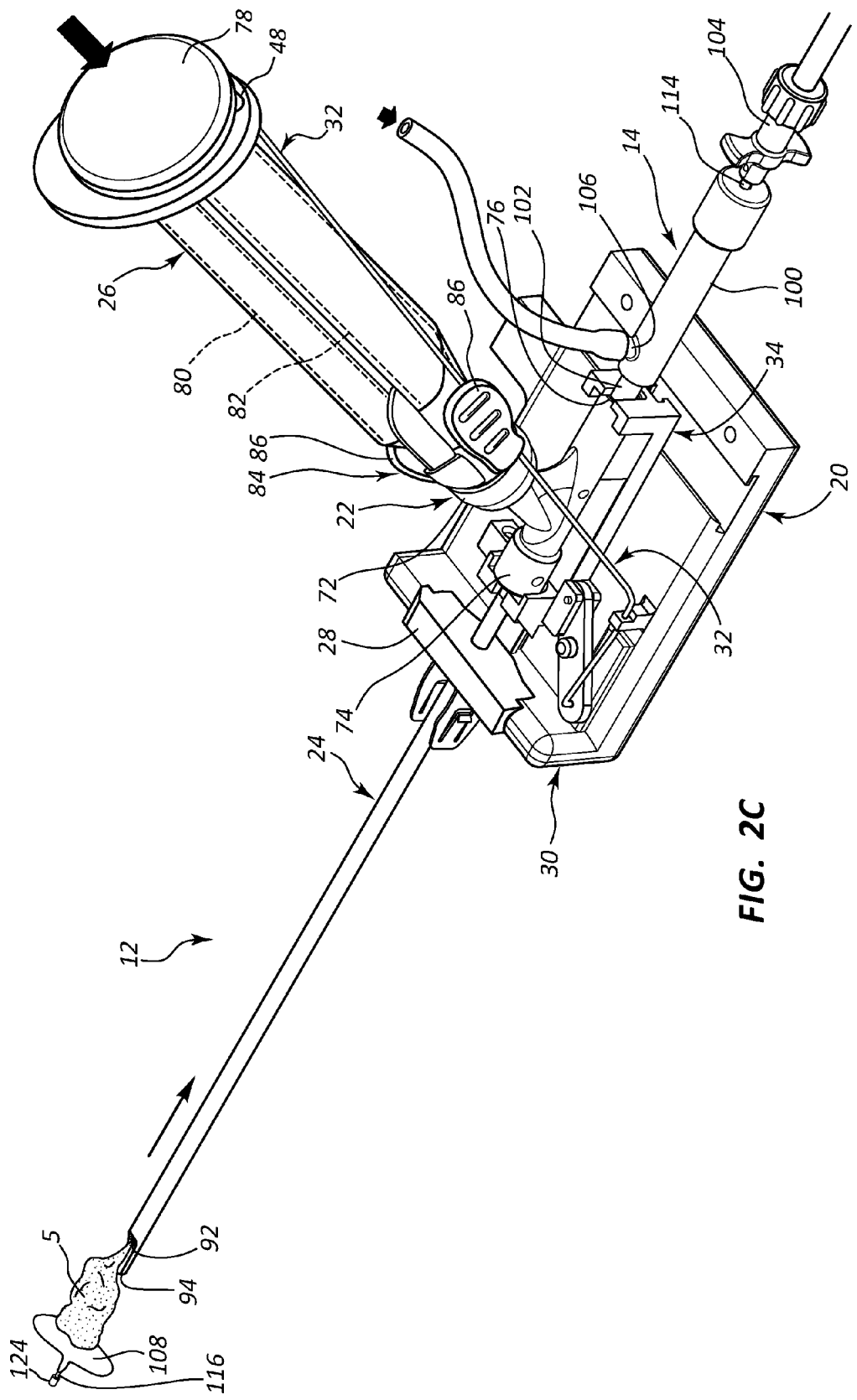
FIG. 2C is a side view of the vascular closure device and balloon location device of FIG. 2A in a second ejection position.

In operation, the retraction assembly 20 maintains the advanced position as shown in FIGS. 2A and 2B until the plunger 78 is advanced into contact with the proximal end 48 of the wire 32. The arrangement shown in FIG. 2A may be referred to as a pre-ejection position wherein the vascular closure device 12 has not yet ejected the sealant at the distal opening 92. The arrangement shown in FIG. 2B may be referred to as a first ejection position wherein the plunger 78 has been advanced enough to eject some of the sealant (a first volume of the sealant) out of the distal opening 92 by the wire 32 has not been actuated. The arrangement of FIG. 2C may be referred to as a second ejection position or a retracted position wherein the plunger 78 contacts the proximal end 48 of wire 32, which rotates lever 52 to retract carriage 50 relative to base 30. The plunger 78 concurrently ejects addition sealant from the distal opening 92 (a second volume of sealant) as the carriage 50 withdraws the delivery tube 24 relative to balloon 108.

Figure 6:
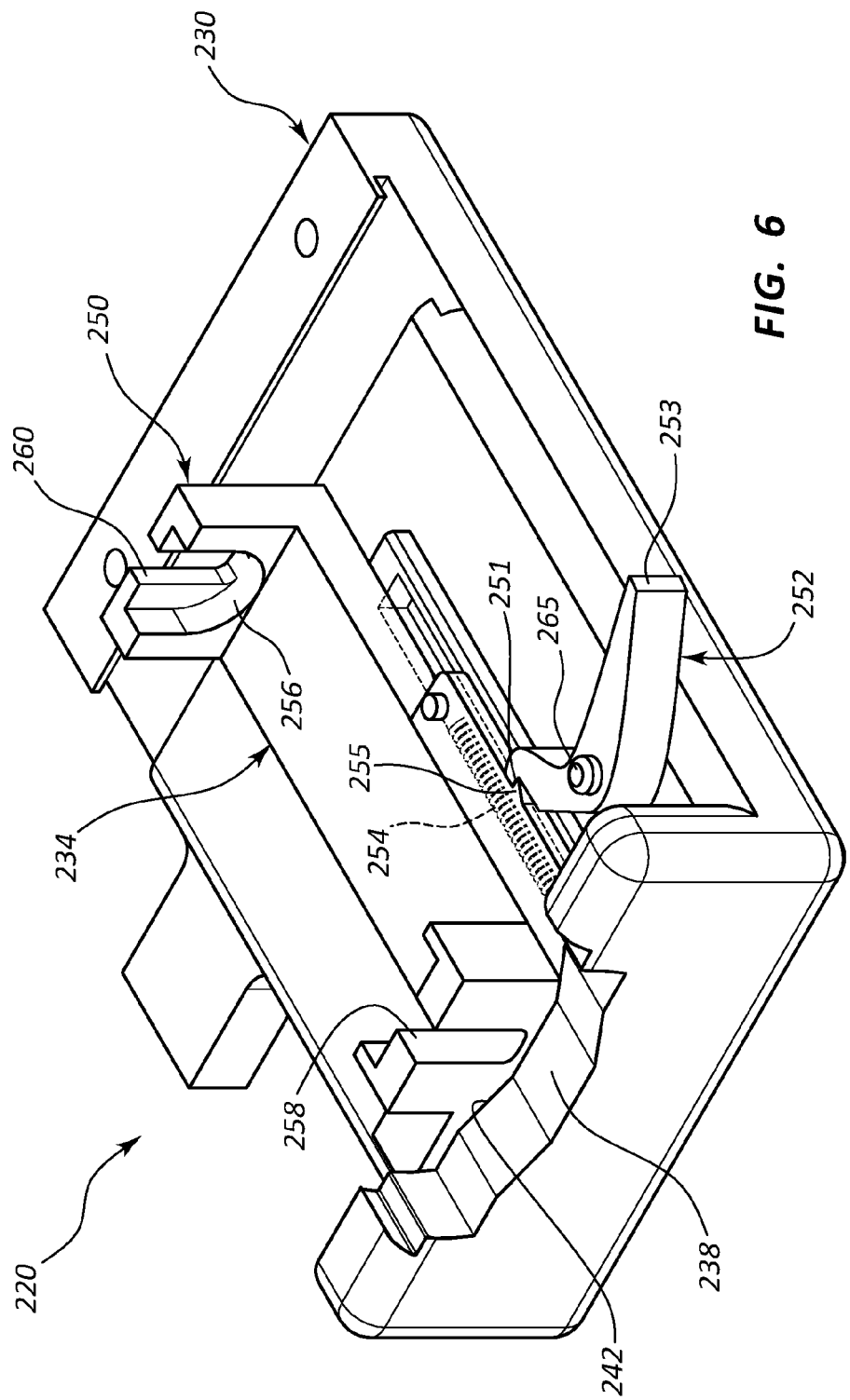
FIG. 6 is a perspective view of another example retraction assembly in a pre-ejection position in accordance with the present disclosure.
Figure 7:
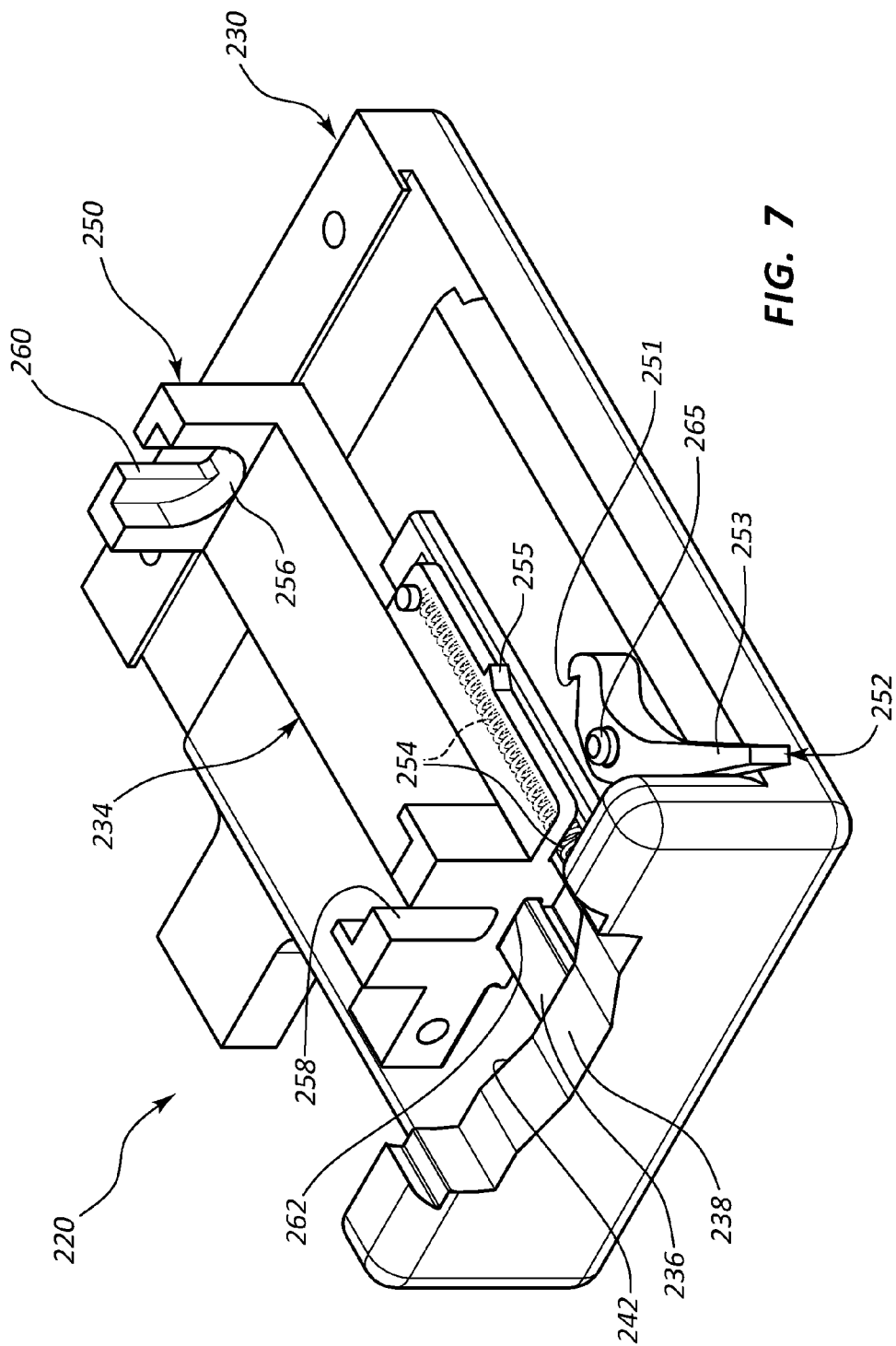
FIG. 7 is a perspective view of the retraction assembly of FIG. 6 in a retracted or second ejection position.
Figure 8:
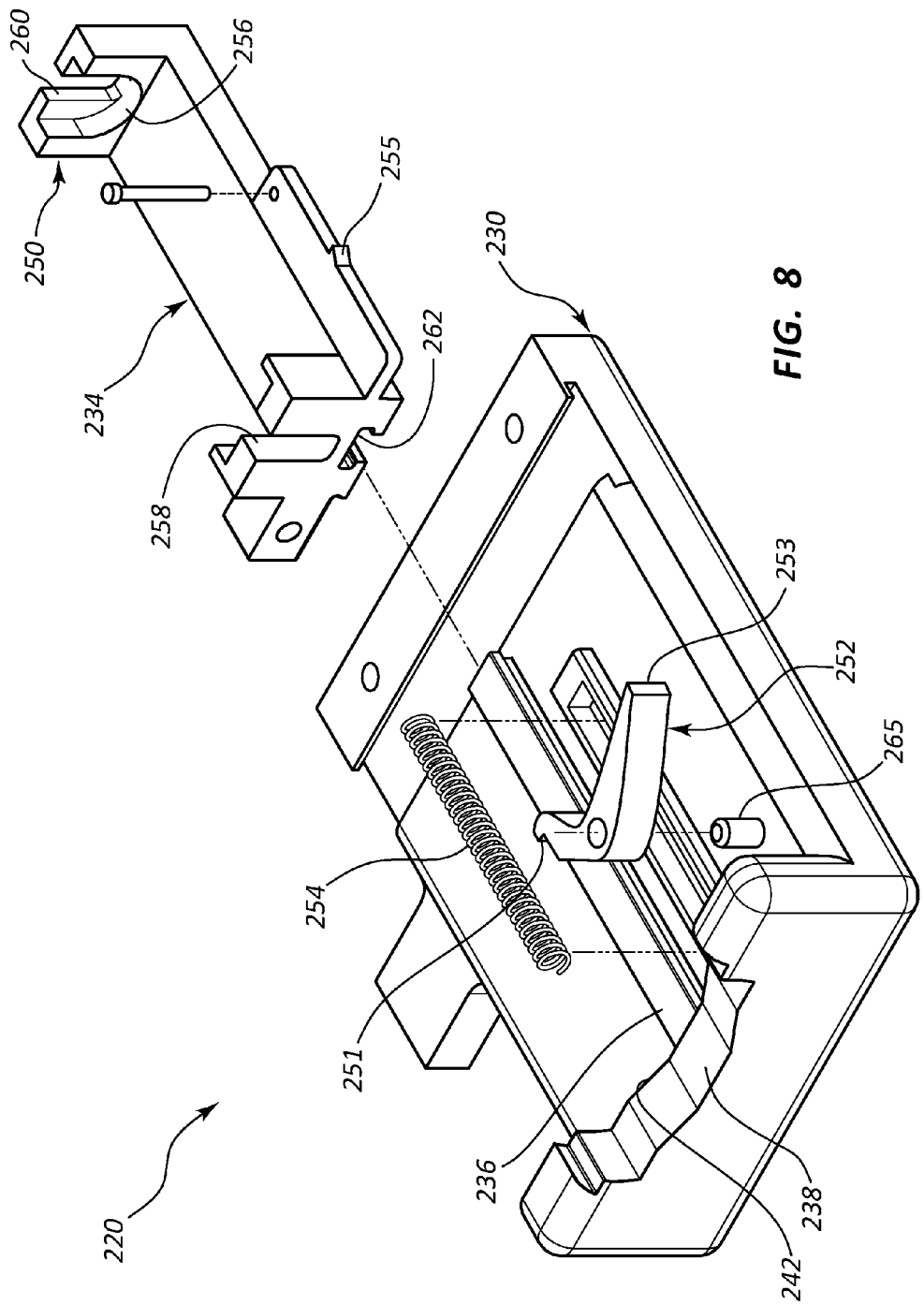
FIG. 8 is an exploded perspective view of the refraction assembly of FIGS. 6 and 7.
Figure 9:
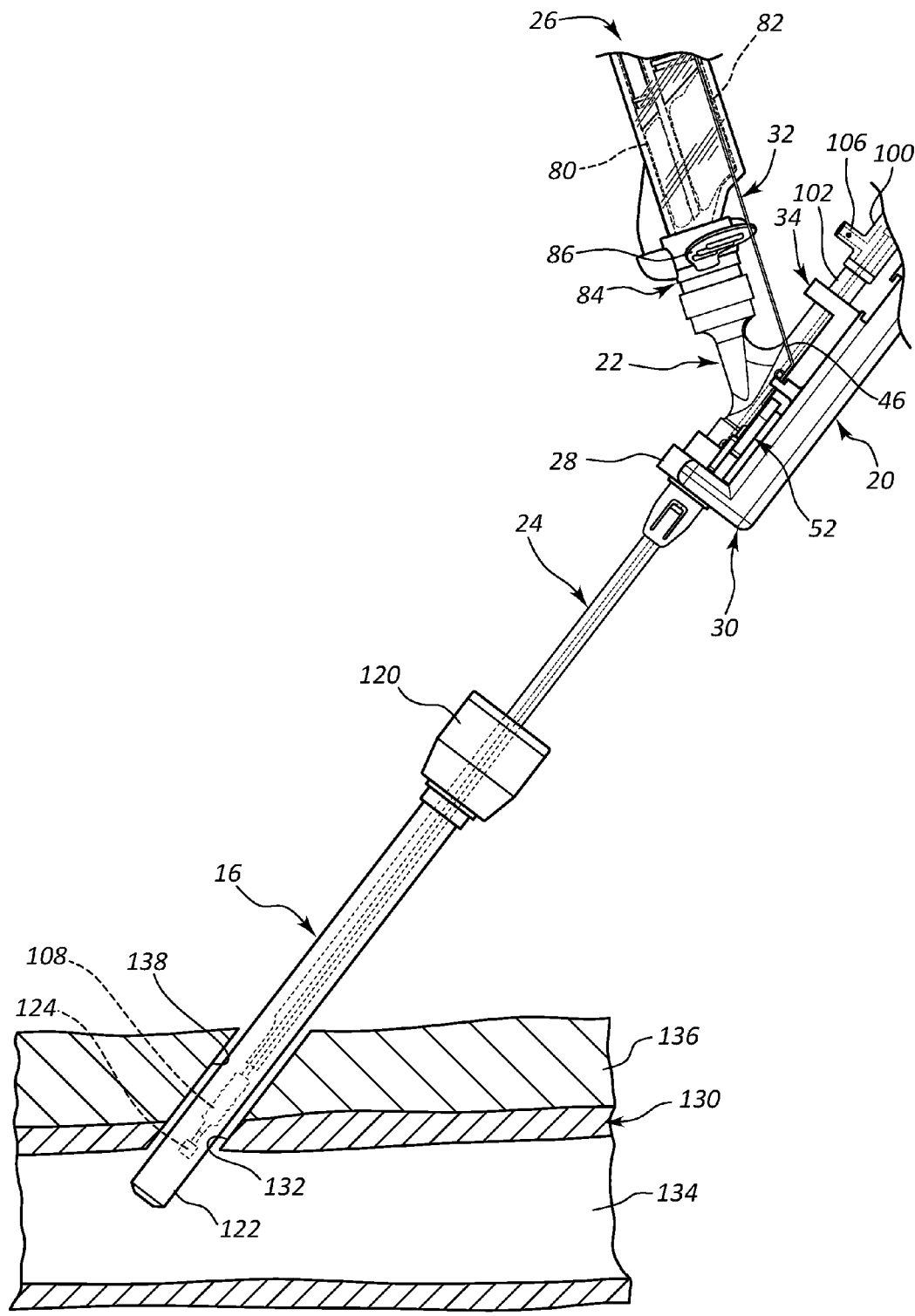
FIGS. 9-13 show steps of sealing a tissue puncture using the vascular closure system of FIG. 1.

Referring now to FIGS. 6-8, another example retraction assembly 220 is shown and described. Retraction assembly 220 includes a base 230 and a carriage assembly 234. The base 230 includes a base track 236, a latch seat 238, and a carriage stop 242. The carriage assembly 234 includes a carriage 250, a release member 252, and a biasing member 254. The carriage 250 may include a manifold seat 256, distal and proximal tube openings 258, 260, and a carriage track 262.

The carriage 250 may be connected to base 230 using base track 236 and carriage track 262. The manifold seat 256 may be configured to secure the manifold 22 to the retraction assembly 220. The distal tube opening 258 is sized to permit insertion of the delivery tube 24 into the retraction assembly 220 for connection to manifold 22. The proximal tube opening 260 is configured for insertion of a portion of the balloon location device 14 through the retraction assembly 220 and into the manifold 22. The latch seat 238 may be configured to support the latch 28, wherein the latch 28 secures the base 230 to the sheath 16.

The release member 252 may be operated to move between a first position shown in FIG. 6 that inhibits longitudinal movement of the carriage 50 relative to base 230, and a released position shown in FIG. 7 in which the carriage 250 is free to move longitudinally relative to base 230. Release member 252 may include a first latch portion 251 that releasably connects to a second latch portion 255 of the carriage assembly. Release member 252 may also include an actuation portion 253 that is arranged to be contacted by an operator's thumb or finger to rotate the release member 252 between the stop and released positions shown in FIGS. 6 and 7, respectively.

When the release member is moved into the released position shown in FIG. 7, the biasing member 254 is able to apply longitudinal force to carriage 250 to retract carriage 250 relative to base 230.

Other arrangements may include different types of release members and biasing members in various configurations. In one example, the release member 252 is constructed as at least one of a push-button, slide, stop, pivot, screw, latch, rotating cam, spring with step lever mechanism, or other mechanical device that holds the carriage 250 in a fixed longitudinal position in one orientation and permits carriage 250 to move longitudinally relative to base 230 in another orientation. Other types of structures besides biasing members (e.g., springs) may be used to apply a force to carriage 250 to provide retraction of carriage 250. In one example, an extension spring may be used in place of a compression spring. Other devices such as coils, spools, or elastic members may be used to apply a force to move carriage 250 relative to base 230.

Referring now to FIGS. 9-13, an example method of sealing a tissue puncture is described using the vascular closure system 10 of FIGS. 1-5. The tissue puncture is a vessel puncture 132 in a vessel 130. The vessel puncture 132 is accessible through a tissue tract 138 in a tissue layer 136. The method may be initiated by inserting the distal end 122 of sheath 16 through the tissue tract 138 and vessel puncture 132 into a vessel lumen 134 of vessel 130. The balloon location device 14 may be inserted through vascular closure device 12. The vascular closure device 12 and balloon location device 14 may be aligned for insertion through hub 120 of sheath 16. The primary sealant device 26 may be pre-mounted to the manifold 22. Alternatively, the primary sealant device 26 may be mounted to manifold 22 in a later step (e.g., after insertion of vascular closure device 12 through sheath 16).

Figure 10:
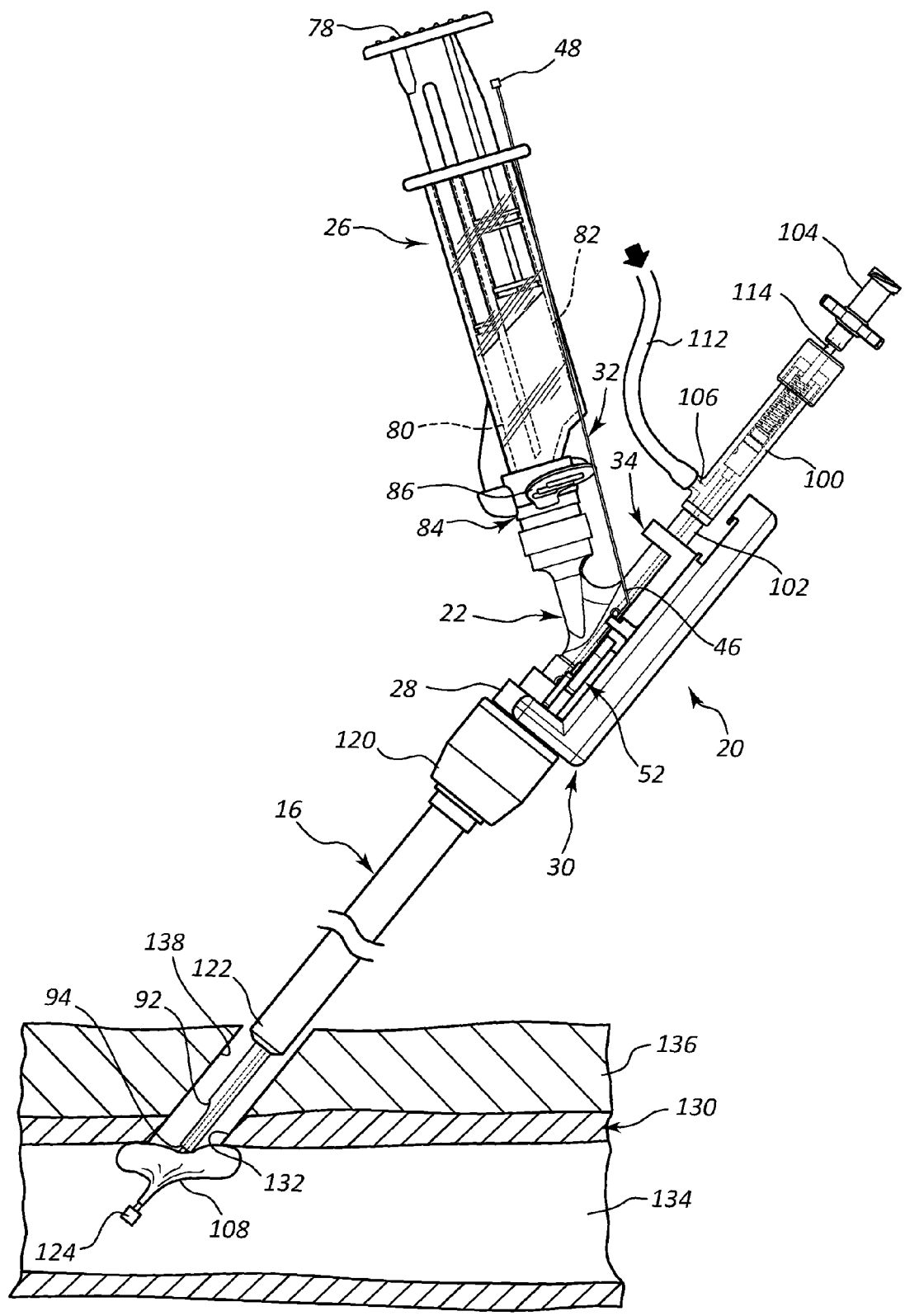

Referring to FIG. 10, the vascular closure device 12 and balloon location device 14 are advanced through sheath 16 until the balloon 108 is positioned within the vessel lumen 134. A volume of inflation fluid may be delivered from an inflation fluid source 112 through the inflation fluid port 106 of balloon location device 14 and to the balloon 108. The inflated balloon 108 may be withdrawn proximally into contact with an inner surface of vessel 130 adjacent to vessel puncture 132 to provide a temporary seal of vessel puncture 132.

Figure 11:
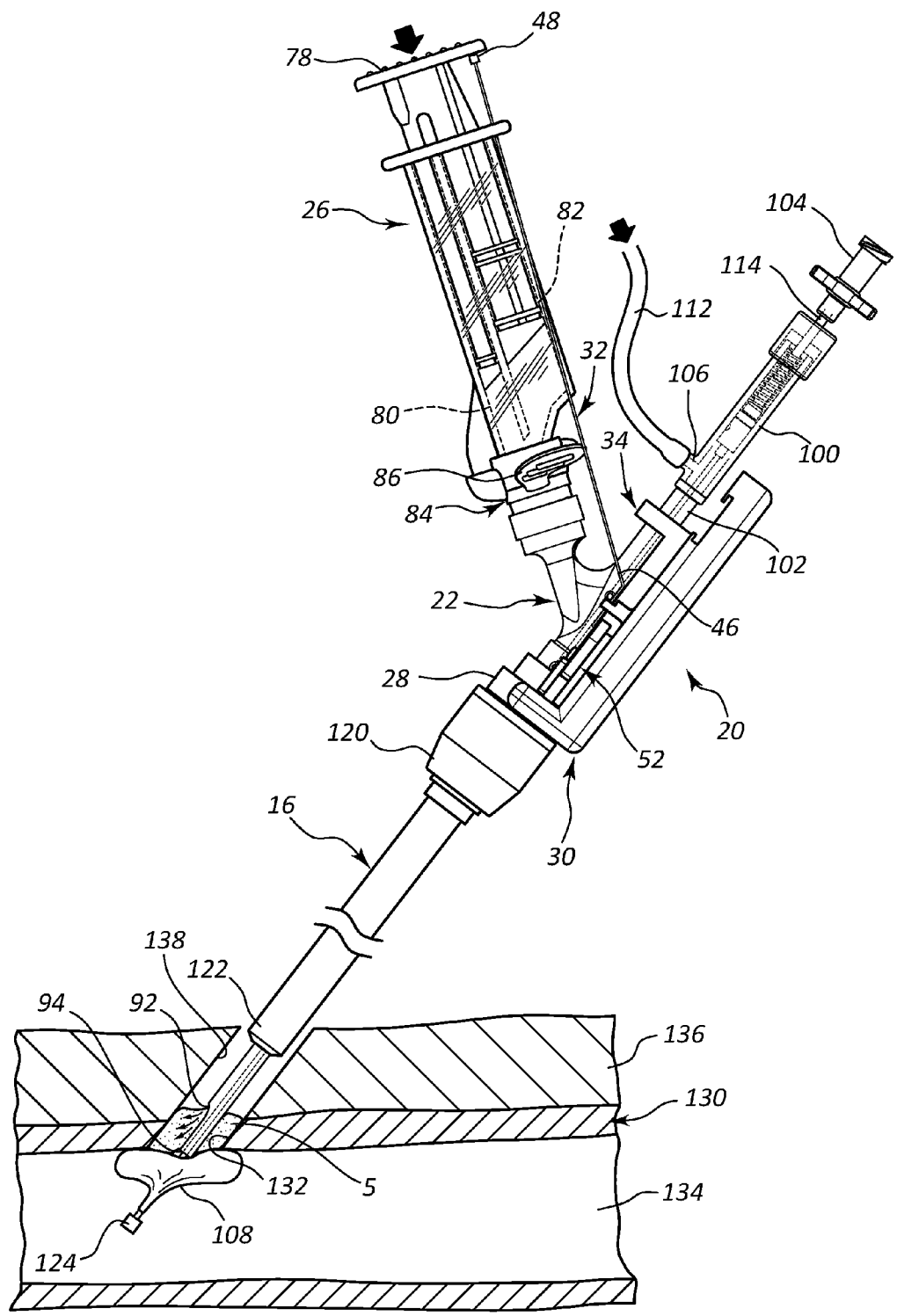

The distal opening 92 of delivery tube 24 may be positioned adjacent to vessel puncture 132 and within tissue tract 138, as shown in FIG. 10. The primary sealant device 26 is operated by advancing plunger 78 to deliver a volume of sealant to the vessel puncture 132, as shown in FIG. 11. The sealant may form a sealant plug 5 after being deposited within tissue tract 138.

Figure 12:
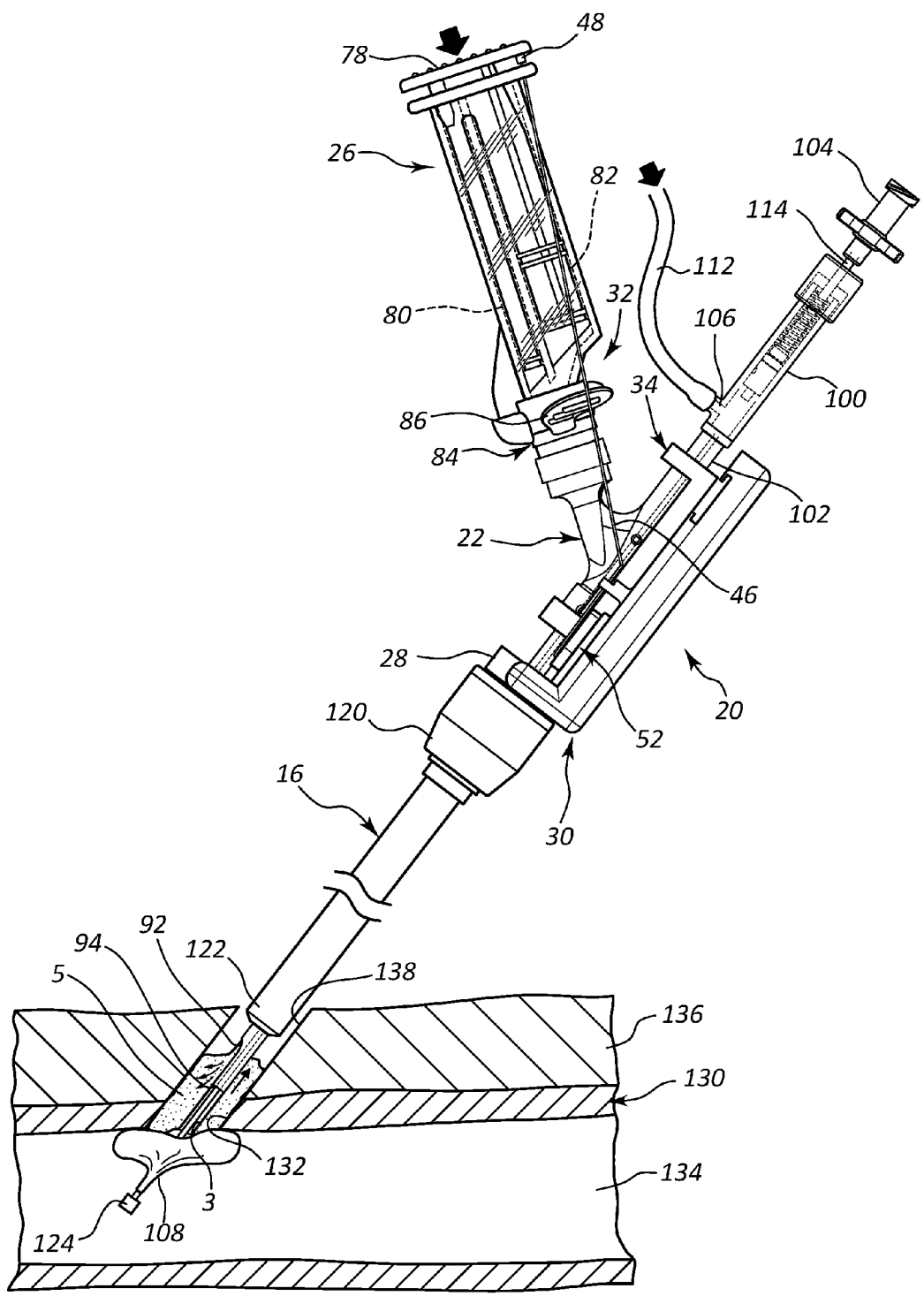

Further advancing the plunger 78 advances wire 32 to automatically retract the carriage 50 relative to base 30 of the retraction assembly 20. The retraction of carriage 50 retracts the distal opening 92 of delivery tube 24 automatically to reposition distal opening 92 at a proximal location within tissue tract 138, as shown in FIG. 12. Further amounts of sealant are delivered to tissue tract 138 as the distal opening 92 is retracted within the tissue tract 138. The sealant plug 5 continues to grow in size and is distributed around the balloon location device 14 and delivery tube 24 as the sealant flows out of the distal opening 92.

Figure 13:
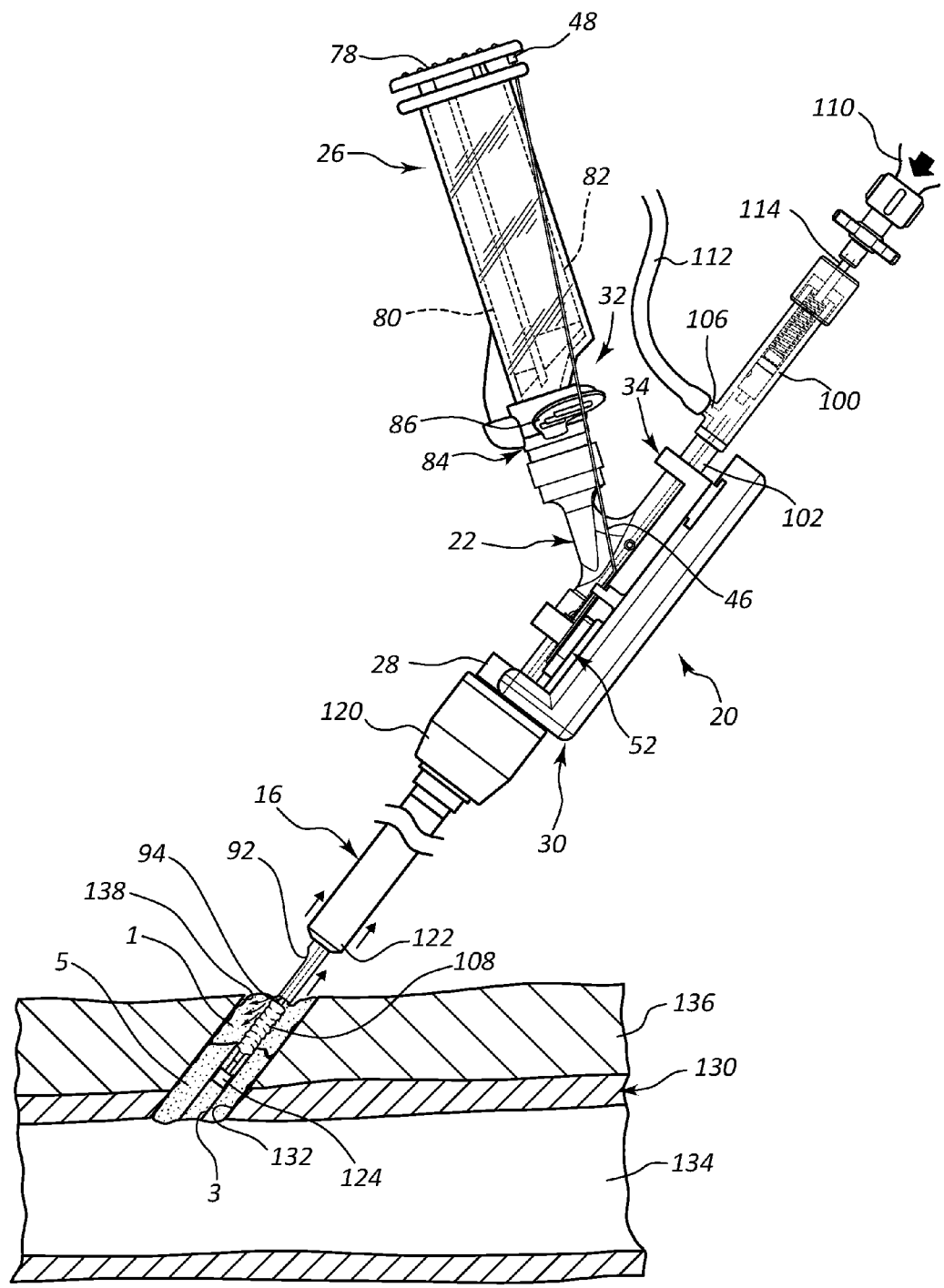

The balloon 108 is then deflated and the vascular closure device 12 and the balloon location device 14 are withdrawn through the sealant plug 5, as shown in FIG. 13. Removing the vascular closure device 12 and balloon location device 14 through the sealant plug 5 may create a sealant tract 3 in the sealant plug 5. The detachable tip 124 may be lodged within the sealant tract 3 and detached from the balloon location device 14 to help close sealant tract 3 and further seal vessel puncture 132.

After detaching the detachable tip 124, a secondary volume of sealant may be delivered through the inner tube 102 into sealant tract 3 using a secondary sealant device 110 attached to the inner tube manifold 104 (see FIG. 13). This secondary volume of sealant may create a secondary sealant plug 1 within sealant tract 3 proximal of the detachable tip 124. In some arrangements, the secondary sealant plug 1 may be used in place of using the detachable tip 124. In other arrangements, the detachable tip 124 may be used independent of providing the secondary sealant plug 1.

Operation of the retraction assemblies disclosed herein may be referred to as automatic or semi-automatic. For example, the retraction assembly may operate to move the outlet opening for a flowable sealant within a tissue tract automatically upon delivering a certain volume of the sealant. In other arrangements, the outlet port for the flowable sealant may move within a tissue tract upon operating an actuator, wherein the actuator initiates a plurality of functions that include automatically moving the outlet port. The automatic moving may occur after a certain volume of the flowable sealant has been delivered to the tissue tract. The actuation may occur manually, such as by an operator flipping a switch or pushing a button, followed by at least some automated operation of the system to move the outlet port. In some arrangements, both manual and automatic operations are used to move the outlet port for the flowable sealant within the tissue tract.

The sealants discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A vessel puncture closure device, comprising:
   a sheath;
   a balloon catheter extending through the sheath, the balloon catheter having an inflatable balloon positioned at a distal end thereof;
   a sealant delivery catheter extending through the sheath, the sealant delivery catheter having a plurality of internal sealant delivery lumens, the plurality of internal sealant delivery lumens configured to deliver a volume of sealant to a vessel puncture, the plurality of internal sealant delivery lumens each having a distal end, at least two of the distal ends having different longitudinal positions along the sealant delivery catheter;
   a carriage assembly comprising a latch and a base, the latch being longitudinally aligned with the balloon catheter and the sealant delivery catheter, the latch being configured to provide temporary attachment of the base to the sheath;
   wherein the sealant delivery catheter is configured to move axially relative to the inflatable balloon, the sheath, and the base between a first position in which the sealant delivery catheter delivers a first volume of sealant to the vessel puncture, and a second position spaced proximal of the first position to deliver a second volume of sealant to the vessel puncture.

2. The vessel puncture closure device of claim 1, further comprising a retraction device interposed between the balloon catheter and sealant delivery catheter to move the sealant delivery catheter between the first and second positions.

3. The vessel puncture closure device of claim 2, wherein the retraction device includes an activator, which when operated causes the retraction device to automatically move the sealant delivery catheter between the first and second positions.

4. The vessel puncture closure device of claim 2, wherein the retraction device includes a biasing member, and releasing the biasing member moves the sealant delivery catheter between the first and second positions.

5. The vessel puncture closure device of claim 2, further comprising a sealant source coupled in flow communication with the sealant delivery catheter, and operating the sealant source to deliver one of the first and second volumes of sealant operates the retraction device.

6. The vessel puncture closure device of claim 5, wherein the sealant source comprises a syringe having a plunger, and operating the plunger to eject at least one of the first and second volumes of sealant into the sealant delivery catheter operates the retraction device.

7. The vessel puncture closure device of claim 2, wherein the balloon catheter comprises a housing, and the retraction device is mounted to the housing.

8. The vessel puncture closure device of claim 1, wherein the sealant delivery catheter includes a distal sealant opening spaced a first predetermined distance from the inflatable balloon in the first position and spaced a second predetermined distance from the inflatable balloon in the second position.

9. The vessel puncture closure device of claim 1, wherein the sealant delivery catheter is advanced over the balloon catheter to the vessel puncture.

10. The vessel puncture closure device of claim 1, further comprising a detachable sealing tip positioned at a distal end of the balloon catheter distal of the inflatable balloon, the detachable sealing tip being detachable within the first volume of sealant upon removal of the balloon catheter from the vessel puncture.

11. A tissue puncture closure device, comprising:
a sheath;
a first catheter extending through the sheath, the first catheter having a balloon positioned at a distal end thereof, the first catheter being insertable through a tissue puncture and configured to inflate the balloon to temporarily seal the tissue puncture internally;
a second catheter extending through the sheath, the second catheter being configured to advance over the first catheter to the tissue puncture, the second catheter having a plurality of sealant delivery lumens, the plurality of sealant delivery lumens being configured to deliver a volume of sealant to seal the tissue puncture externally, the plurality of sealant delivery lumens each having distal openings positioned at different longitudinal positions on the second catheter;
a retraction device having a carriage assembly, a latch, and a base, the latch providing temporary attachment of the base to the sheath, the second catheter being mounted to the carriage assembly, the retraction device being operable between the first and second catheters to automatically move a distal opening of the second catheter relative to the sheath between a first axial position relative to the balloon and a second axial position spaced further from the balloon than the first axial position, the carriage assembly being configured to guide longitudinal movement of the second catheter relative to the base between the first and second axial positions.

12. The tissue puncture closure device of claim 11, wherein the retraction device further comprises a trigger operable to actuate the retraction device.

13. The tissue puncture closure device of claim 11, further comprising a sealant source configured to deliver a first volume of sealant to the tissue puncture when the distal opening is in the first axial position, and to deliver a second volume of sealant to the tissue puncture when the distal opening is in the second axial position.

14. The tissue puncture closure device of claim 13, wherein operating the sealant source actuates a trigger.

15. The tissue puncture closure device of claim 13, wherein the sealant source operates to provide a continuous flow of the first and second volumes of sealant.

* * * * *